(12) United States Patent
Tang et al.

(10) Patent No.: US 11,564,864 B2
(45) Date of Patent: Jan. 31, 2023

(54) GRAPHENE NANO-STEAM GENERATOR

(71) Applicant: Hangzhou Tsingke Energy and Environmental Technology Co., Ltd., Hangzhou (CN)

(72) Inventors: Feng Tang, Hangzhou (CN); Feng Jiang, Hangzhou (CN); Chao Yuan, Hangzhou (CN)

(73) Assignee: Hangzhou Tsingke Energy and Environmental Technology Co., Ltd., Hangzhou (CN)

( * ) Notice: Subject to any disclaimer, the term of this patent is extended or adjusted under 35 U.S.C. 154(b) by 890 days.

(21) Appl. No.: 16/473,271

(22) PCT Filed: Oct. 29, 2018

(86) PCT No.: PCT/CN2018/112284
§ 371 (c)(1),
(2) Date: Jun. 25, 2019

(87) PCT Pub. No.: WO2019/227840
PCT Pub. Date: Dec. 5, 2019

(65) Prior Publication Data
US 2020/0315912 A1    Oct. 8, 2020

(51) Int. Cl.
*A61H 33/06* (2006.01)
*B01J 19/08* (2006.01)
(Continued)

(52) U.S. Cl.
CPC ........... *A61H 33/06* (2013.01); *A61M 11/001* (2014.02); *B01J 19/088* (2013.01);
(Continued)

(58) Field of Classification Search
CPC .............. A61H 33/06; A61H 2033/068; A61H 2201/105; A61H 1/00; A61M 2210/04;
(Continued)

(56) References Cited

U.S. PATENT DOCUMENTS

2014/0313636 A1* 10/2014 Tour ........................ C01B 32/16
423/447.2

FOREIGN PATENT DOCUMENTS

| CN | 2442668 Y | * | 8/2001 | ............. A61H 33/12 |
| CN | 103208373 A | * | 7/2013 | |

OTHER PUBLICATIONS

CN2442668Y Bib Translated (Year: 2001).*
(Continued)

*Primary Examiner* — Ellen M Mcavoy
*Assistant Examiner* — Chantel L Graham

(57) ABSTRACT

A graphene nano-steam generator and a beauty instrument are provided. The graphene nano-steam generator includes a coarse steam channel, a nano-steam channel and a high-voltage power supply device. The coarse steam channel is connected to a coarse steam manufacturing device and the nano-steam channel. The coarse steam channel is provided with a steam sieving device, and an end of the coarse steam channel is provided with a first electrode and a second electrode. The high-voltage power supply device is coupled to the first electrode and the second electrode. The high-voltage power supply device supplies high-voltage electricity to the first electrode and the second electrode, and forms a high-voltage arc discharge between the first electrode and the second electrode, thus the coarse steam molecular group flowing through is ionized by the high-voltage arc to generate a large amount of active nano-scale steam to be flowed out from the nano-steam channel.

8 Claims, 3 Drawing Sheets

(51) Int. Cl.
*A61M 11/00* (2006.01)
*B82Y 5/00* (2011.01)
(52) U.S. Cl.
CPC .. *A61H 2033/068* (2013.01); *A61H 2201/105* (2013.01); *A61M 2205/0233* (2013.01); *A61M 2210/04* (2013.01); *B01J 2219/00763* (2013.01); *B01J 2219/025* (2013.01); *B01J 2219/0809* (2013.01); *B01J 2219/0839* (2013.01); *B01J 2219/0845* (2013.01); *B82Y 5/00* (2013.01)
(58) Field of Classification Search
CPC ........ A61M 11/001; A61M 2205/0233; A61M 2210/005; A61M 35/30; A61M 37/00; B01J 19/088; B01J 19/2495; B01J 2219/00763; B01J 2219/025; B01J 2219/0809; B01J 2219/0839; B01J 2219/0845; B82Y 5/00
See application file for complete search history.

(56) References Cited

OTHER PUBLICATIONS

CN2442668Y Claims Translated (Year: 2001).*
CN2442668Y Description Translated (Year: 2001).*
CN103208373A Bib Translated (Year: 2013).*
CN103208373A Claims Translated (Year: 2013).*
CN103208373A Description Translated (Year: 2013).*

* cited by examiner

GRAPHENE NANO-STEAM GENERATOR

FIELD OF THE DISCLOSURE

The present invention relates to a graphene nano-steam generator and a beauty instrument thereof, belonging to the fields of hydrating beauty, humidification, recuperation and nursing, in particular to the fields of beauty, humidification, recuperation and nursing through manufacturing nano-steam by high-voltage discharge.

BACKGROUND OF THE INVENTION

Hydrating is the basis for skin care. The existing hydrating beauty instrument usually generates water mist by ultrasonic vibration or high-temperature heating, and sprays the water mist through a nozzle to achieve hydrating effect. However, the particle size of the generated water mist is mostly in a micrometer-order, and the particle size is too large, which is difficult to be absorbed by skin. Furthermore, the water mist has not been sterilized, which often has a negative effect on the skin.

Nano-steam has many advantages, such as biological activity, small particle size, stable performance, hydrating beauty, etc., and has gradually become a research hotspot in the fields of beauty, recuperation, and nursing. The existing high-voltage discharge type nano-steam generators mainly have the following two drawbacks:

(1) In a high-humidity environment, the discharge electrodes accumulate water or are oxidized, causing the electric field to deteriorate, thereby causing the discharge to be unstable or terminated, such that the nano-steam cannot be stably produced.

(2) In order to avoid water accumulation or oxidation of the discharge electrodes, a complicated water absorbing device is required or expensive metal material is used, which results in a large increase in manufacturing process complexity, defective rate, and manufacturing cost.

SUMMARY OF THE INVENTION

In order to solve the above problems, it is an object of the present invention to provide a graphene nano-steam generator and a beauty instrument having the same thereof.

According to an exemplary embodiment, a graphene nano-steam generator is provided. The graphene nano-steam generator includes a coarse steam channel, a nano-steam channel and a high-voltage power supply device. The coarse steam channel is respectively connected to a coarse steam manufacturing device and the nano-steam channel. The coarse steam channel is provided with a steam sieving device, and an end of the coarse steam channel is provided with a first electrode and a second electrode respectively fixed to an electrode fixing member. The high-voltage power supply device is coupled to the first electrode and the second electrode. The high-voltage power supply device supplies high-voltage electricity to the first electrode and the second electrode, and forms a high-voltage arc discharge between the first electrode and the second electrode, thus the coarse steam molecular group flowing through is ionized by the high-voltage arc to generate a large amount of active nano-scale steam to be flowed out from the nano-steam channel.

In one embodiment, electrode tips of the first electrode and the second electrode are made of a plurality of graphene, fullerene or carbon fiber filaments/bundles.

In one embodiment, a central axis of the first electrode and a central axis of the second electrode are located on an identical plane or on different planes.

In one embodiment, an amount of electrode tips of the first electrode is one or more, and an amount of electrode tips of the second electrode is one or more.

In one embodiment, the graphene nano-steam generator further includes an intermediate conductor, disposed between the first electrode and the second electrode.

In one embodiment, the intermediate conductor is spaced at a predetermined distance from the first electrode and the second electrode, respectively. A central axis of the intermediate conductor and the central axes of the first electrode and the second electrode are located on the same plane, or the central axis of the intermediate conductor is perpendicular to the plane on which the central axes of the first electrode and the second electrode located.

In one embodiment, the intermediate conductor has a cylindrical shape, an I-shape, a cross shape, a square, a sheet shape, a ring shape or a tubular shape.

In one embodiment, all or part of the intermediate conductor is made of graphene, fullerene, carbon fiber, zinc, iron, platinum, titanium, copper, gold or silver.

In one embodiment, at least one of the first electrode, the second electrode, the intermediate conductor and the electrode fixing member is covered with felt or nonwoven fabrics.

According to another exemplary embodiment, a beauty instrument having a graphene nano-steam generator is provided. The graphene nano-steam generator includes a coarse steam channel, a nano-steam channel and a high-voltage power supply device. The coarse steam channel is respectively connected to a coarse steam manufacturing device and the nano-steam channel. The coarse steam channel is provided with a steam sieving device, and an end of the coarse steam channel is provided with a first electrode and a second electrode respectively fixed to an electrode fixing member. The high-voltage power supply device is coupled to the first electrode and the second electrode. The high-voltage power supply device supplies high-voltage electricity to the first electrode and the second electrode, and forms a high-voltage arc discharge between the first electrode and the second electrode, thus the coarse steam molecular group flowing through is ionized by the high-voltage arc to generate a large amount of active nano-scale steam to be flowed out from the Nano-steam channel.

In one embodiment, electrode tips of the first electrode and the second electrode are made of a plurality of graphene, fullerene or carbon fiber filaments/bundles.

In one embodiment, a central axis of the first electrode and a central axis of the second electrode are located on an identical plane or on different planes.

In one embodiment, an amount of electrode tips of the first electrode is one or more, and an amount of electrode tips of the second electrode is one or more.

In one embodiment, the graphene nano-steam generator further includes an intermediate conductor, disposed between the first electrode and the second electrode.

In one embodiment, the intermediate conductor is spaced at a predetermined distance from the first electrode and the second electrode, respectively. A central axis of the intermediate conductor and the central axes of the first electrode and the second electrode are located on the same plane, or the central axis of the intermediate conductor is perpendicular to the plane on which the central axes of the first electrode and the second electrode located.

In one embodiment, the intermediate conductor has a cylindrical shape, an I-shape, a cross shape, a square, a sheet shape, a ring shape or a tubular shape.

In one embodiment, all or part of the intermediate conductor is made of graphene, fullerene, carbon fiber, zinc, iron, platinum, titanium, copper, gold or silver.

In one embodiment, at least one of the first electrode, the second electrode, the intermediate conductor and the electrode fixing member is covered with felt or nonwoven fabrics.

The graphene nano-steam generator and the beauty instrument having the same are disclosed in the embodiments of the present invention. The steam produced by a coarse steam manufacturing device flows into the coarse steam channel, wherein large-sized water droplets are filtered by the steam sieving device, and the remaining steam continues to flow upward. When the steam is flowing between the first electrode and the second electrode, a high-voltage arc is formed between the first electrode and the intermediate conductor and a high-voltage arc is formed between the intermediate conductor and the second electrode since a high-voltage electric field is supplied to the first electrode and the second electrode. Due to the strong discharge effect, the steam water molecule group is ionized by the high-voltage arc to generate a large amount of nano-sized steam.

In one embodiment, the first electrode and the second electrode are made of graphene, fullerene, or carbon fiber filaments/bundles, etc. Graphene, fullerene, and carbon fiber filaments/bundles and the like have advantages of good air circulation, being less likely to accumulate water, a large number of gaps, good oxidation resistance, aging resistance, superconductivity and stable resistance value, so they can stably discharge in a high-humidity environment and can manufacture a large amount of nano-steam continuously and stably.

BRIEF DESCRIPTION OF THE DRAWINGS

Aspects of the present disclosure are best understood from the following detailed description when read the accompanying figures. It is noted that, in accordance with the standard practice in the industry, various features are not drawn to scale. In fact, the dimensions of the various features may be arbitrarily increased or reduced for clarity of discussion.

Figure 1A:
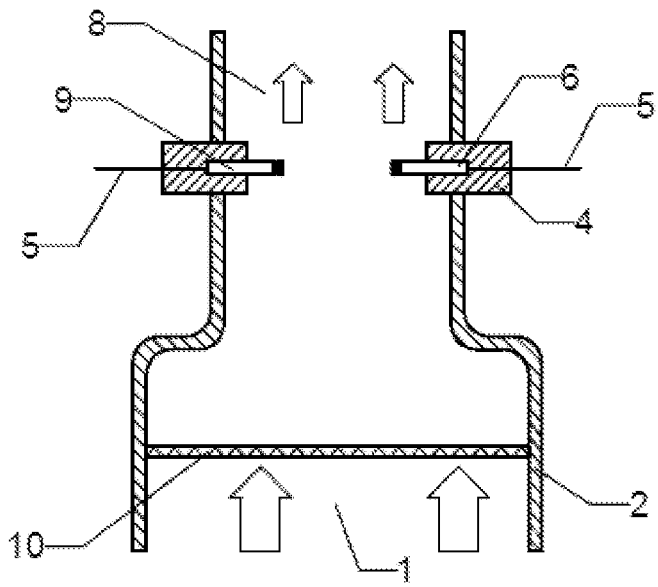
FIG. 1A is a structural diagram of a graphene nano-steam generator according to a first embodiment of the present invention.

The serial numbers in the figures:
1 Coarse steam channel
2 Steam pipe
3 Fixing frame
4 Electrode fixing member
5 Conducting wire
6 First electrode
7 Intermediate conductor
8 nano-steam channel
9 Second electrode
10 Steam sieving device
11 Electrode tip
12 High-voltage power supply device

DESCRIPTION OF THE PREFERRED EMBODIMENTS

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Please refer to FIG. 1A. FIG. 1A is a structural diagram of a graphene nano-steam generator according to a first embodiment of the present invention. The graphene nano-steam generator includes a coarse steam channel 1 and a nano-steam channel 8, wherein the coarse steam channel 1 is respectively connected to a coarse steam manufacturing device (not shown in FIG. 1A) and the nano-steam channel 8. The coarse steam channel 1 is provided with a steam sieving device 10, and an end of the coarse steam channel 1 is provided with a first electrode 6 and a second electrode 9 respectively fixed to an electrode fixing member 4. The graphene nano-steam generator further includes a high-voltage power supply device 12 coupled to the first electrode 6 and the second electrode 9. The high-voltage power supply device 12 supplies high-voltage electricity to the first electrode 6 and the second electrode 9, and forms a high-voltage arc discharge between the first electrode 6 and the second electrode 9, thus the coarse steam molecular group flowing through is ionized by the high-voltage arc to generate a large amount of active nano-sized steam to be flowed out from the nano-steam channel 8.

Specifically, using the first electrode 6 and the second electrode 9 as a boundary, the inner walls of the steam pipe form the coarse steam channel 1 and the nano-steam channel 8, respectively.

In one embodiment, the first electrode 6 and the second electrode 9 are made of graphene, fullerene or carbon fiber filaments/bundles, etc. By using the stable discharge performance of graphene, fullerene, carbon fiber filaments/bundles and the like in a high-humidity environment, ordinary steam is produced into active nano-sized steam.

In one embodiment, a central axis of the first electrode 6 and a central axis of the second electrode 9 are located on an identical plane or on different planes.

In one embodiment, an amount of electrode tips 11 of the first electrode 6 may be one or more, and an amount of electrode tips 11 of the second electrode 9 may be one or more.

The steam sieving device 10 is configured to filter out large-sized steam droplets, wherein finer water mist is initially screened, and large water droplets are prevented from interfering with the stability of the high-voltage discharge. The first electrode 6 and the second electrode 9 are symmetrically disposed and are respectively fixed to the steam pipe 2 by the electrode fixing member 4.

Figure 2A:
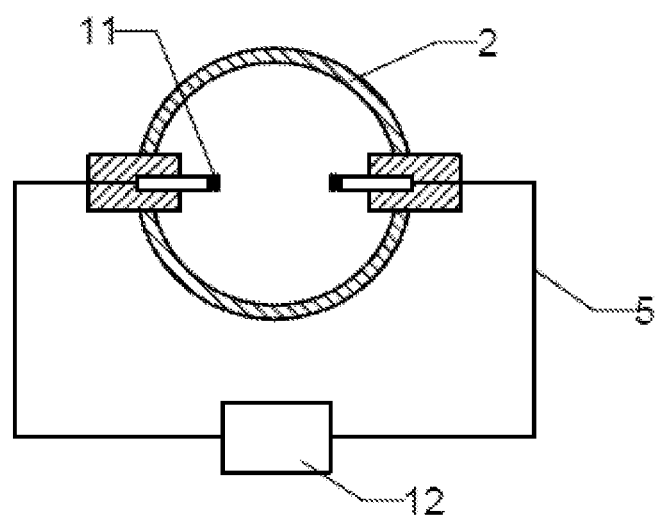
FIG. 2A is a top plan view of a graphene nano-steam generator according to a first embodiment of the present invention.

As shown in FIG. 1A and FIG. 2A, the first electrode 6 and the second electrode 9 are respectively connected to the high-voltage power supply device 12 through a conducting wire 5. The high-voltage power supply device 12 supplies high-voltage electricity to the first electrode 6 and the second electrode 9, and a high-voltage arc discharge is formed between the first electrode 6 and the second electrode 9.

Figure 1B:
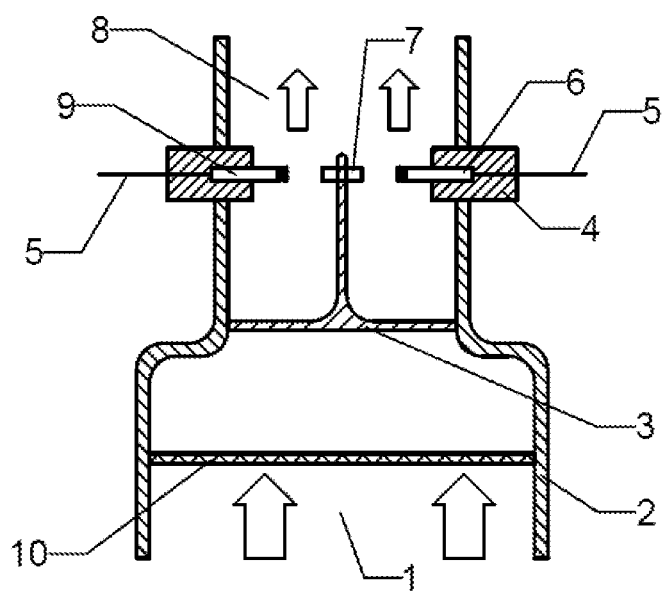
FIG. 1B is a structural diagram of a graphene nano-steam generator with an intermediate conductor according to a second embodiment of the present invention.
Figure 2B:
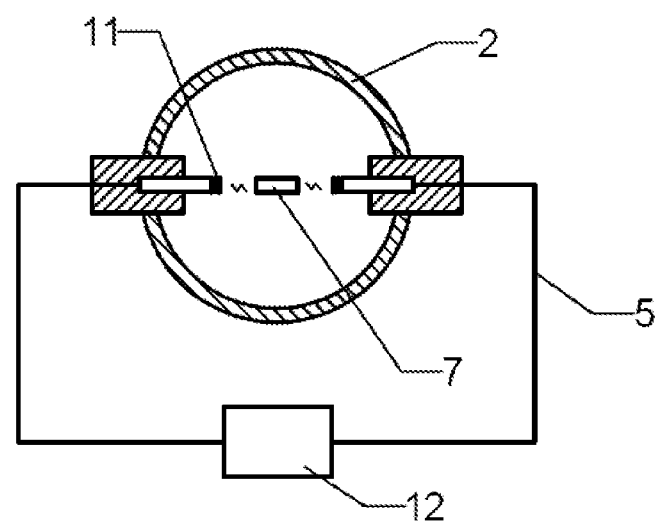
FIG. 2B is a top plan view of a graphene nano-steam generator with an intermediate conductor according to a second embodiment of the present invention.

Please refer to FIG. 1B and FIG. 2B. FIG. 1B is a structural diagram of a graphene nano-steam generator with an intermediate conductor according to a second embodiment of the present invention, and FIG. 2B is a top plan view of a graphene nano-steam generator with an intermediate conductor according to a second embodiment of the present invention. The graphene nano-steam generator further includes an intermediate conductor 7 disposed between the first electrode 6 and the second electrode 9. The first electrode 6 and the second electrode 9 are symmetrically disposed on the cross section of the steam pipe 2, and the intermediate conductor 7 is disposed at the center of the steam pipe and between the first electrode 6 and the second electrode 9 without contacting each other. The intermediate conductor 7 is used to segment the high-voltage discharge and extend the discharge electric field to reduce the voltage required for the high-voltage discharge, which increases the quantity and efficiency of manufacturing the nano-steam.

In one embodiment, the intermediate conductor 7 is fixed between the first electrode 6 and the second electrode 9 by a fixing frame 3, and the intermediate conductor 7 is not connected to the first electrode 6 or the second electrode 9. The central axis of the intermediate conductor 7 and the central axes of the first electrode 6 and the second electrode 9 are located on the same plane, or the central axis of the intermediate conductor 7 is perpendicular to the plane formed by the central axes of the first electrode 6 and the second electrode 9.

The steam produced by the coarse steam manufacturing device flows into the coarse steam channel 1. The large-sized water droplets are first filtered by the steam sieving device 10, and the remaining steam continues to flow upward. When the steam is flowing between the first electrode 6 and the second electrode 9, a high-voltage arc is formed between the first electrode 6 and the intermediate conductor 7 and a high-voltage arc is formed between the intermediate conductor 7 and the second electrode 9 since a high-voltage electric field is supplied to the first electrode 6 and the second electrode 9. Due to the strong discharge effect, the steam water molecule group is ionized by the high-voltage arc to generate a large amount of nano-sized steam.

The coarse steam manufacturing device may be a high-temperature heating steam manufacturing device, or a device for producing steam by means of ultrasonic waves, Venturi effects, or the like.

In one embodiment, the electrode tips 11 of the first electrode 6 and the second electrode 9 are made of a plurality of graphene, fullerene, or carbon fiber filaments/bundles, and the like with a number of certain gaps. Graphene, fullerene, and carbon fiber filaments/bundles have advantages of good air circulation, being less likely to accumulate water, a large number of gaps, good oxidation resistance, aging resistance, superconductivity and stable resistance value, so they can stably discharge in a high-humidity environment and can manufacture a large amount of nano-steam continuously and stably.

The length of the electrode tips 11 of the first electrode 6 and the second electrode 9 is preferably 0.1 to 3 mm.

The intermediate conductor 7 may be a cylindrical shape, wherein the central axis of the intermediate conductor 7 is located on the central axes of the first electrode 6 and the second electrode 9, or the central axis of the intermediate conductor 7 is perpendicular to the plane formed by the central axes of the first electrode 6 and the second electrode 9. The intermediate conductor 7 is preferably made of the corrosion-resistant conductive material, which may be (partially) made of neutral substances, such as graphene, fullerene, carbon fiber, etc.; or may be (partially) made of reducing substances, such as zinc, iron, platinum, titanium, etc.; or may also be (partially) made of substances having bactericidal actions, such as zinc, copper, gold, silver, and the like.

The electrode fixing member 4 and the fixing frame 3 are made of the high-temperature resistant insulating material.

In one embodiment, an amount of the electrode tips 11 of the first electrode 6 may be one or more, and an amount of the electrode tips 11 of the second electrode 9 may be one or more.

In one embodiment, the intermediate conductor 7 may be of various shapes, such as cylindrical, I-shape, cross, square, sheet, ring-shape or tubular. The central axis of the intermediate conductor 7 may be on the same line of the center axes of the first electrode 6 and the second electrode 9, or may be perpendicular to the center axes of the first electrode 6 and the second electrode 9. Or an angle may be formed between the central axis of the intermediate conductor 7 and the center axes of the first electrode 6 and the second electrode 9.

Figure 3:
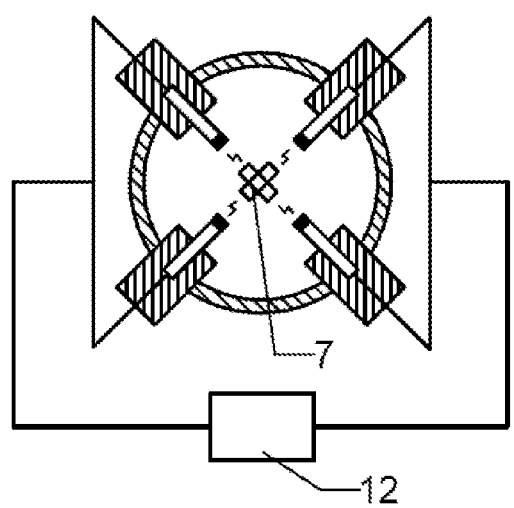
FIG. 3 is a structural diagram of a multi-electrode discharge graphene nano-steam generator according to a third embodiment of the present invention.

Please refer to FIG. 3. FIG. 3 is a structural diagram of a multi-electrode discharge graphene nano-steam generator according to a third embodiment of the present invention. As shown in FIG. 3, the nano-steam generator has a pair of the first electrodes 6 in paralleland a pair of the second electrodes 9 in parallel, and the intermediate conductor 7 is in a cross shape.

In one embodiment, the first electrodes 6 and the second electrodes 9 are in the same form or different forms.

In one embodiment, the central axes of the first electrodes 6 and the second electrodes 9 are located on the same plane or on different planes.

In one embodiment, the intermediate conductor 7 may be omitted, and only the first electrodes 6 and the second electrodes 9 are disposed. The first electrodes 6 and the second electrodes 9 may be respectively disposed on the cross-section of the steam pipe 2, for example, the pair of first electrodes 6 are respectively fixed to both side of the cross-section of the steam pipe 2, and the pair of second electrodes 9 are fixed to the central axis of the steam pipe 2.

In one embodiment, at least one of the first electrode 6, the electrode 9, the intermediate conductor 7, and the electrode fixing member 4 is covered with absorbent and breathable materials, such as felt or nonwoven fabrics, to further enhance the stability of the high-voltage discharge.

In one embodiment, the steam sieving device 10 may be omitted, wherein large-sized water droplets may be prevented from flowing upward by heightening the coarse steam channel 1 or by changing the direction of steam flow.

According to another embodiment of the present invention, a beauty instrument using the graphene nano-steam generator of any one of the foregoing embodiments is provided.

The embodiments of the present invention can stably discharge in a high-humidity environment, and can manufacture a large amount of nano-steam continuously and stably. The present invention has a simple manufacturing process, low manufacturing cost, and convenient large-scale industrial production.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A graphene Nano-steam generator, comprising:
   a coarse steam channel and a Nano-steam channel, wherein the coarse steam channel is respectively connected to a coarse steam manufacturing device and the Nano-steam channel; the coarse steam channel is provided with a steam sieving device, and an end of the coarse steam channel is provided with a first electrode and a second electrode respectively fixed to an electrode fixing member;
   a high-voltage power supply device, coupled to the first electrode and the second electrode; and
   an intermediate conductor, disposed between the first electrode and the second electrode;
   wherein the intermediate conductor is spaced at a predetermined distance from the first electrode and the second electrode, respectively;
   wherein the high-voltage power supply device supplies high-voltage electricity to the first electrode and the second electrode, and forms a high-voltage arc discharge between the first electrode and the second electrode, and a coarse steam molecular group flowing through is ionized by the high-voltage arc to generate a large amount of active nano-scale steam to be flowed out from the Nano-steam channel.

2. The graphene Nano-steam generator in claim 1, wherein electrode tips of the first electrode and the second electrode are made of a plurality of graphene, fullerene or carbon fiber filaments/bundles.

3. The graphene Nano-steam generator in claim 2, wherein a central axis of the first electrode and a central axis of the second electrode are located on an identical plane or on different planes.

4. The graphene Nano-steam generator in claim 1, wherein an amount of electrode tips of the first electrode is one or more, and an amount of electrode tips of the second electrode is one or more.

5. The graphene Nano-steam generator in claim 1, wherein a central axis of the intermediate conductor and the central axes of the first electrode and the second electrode arc located on the same plane, or the central axis of the intermediate conductor is perpendicular to the plane on which the central axes of the first electrode and the second electrode located.

6. The graphene Nano-steam generator in claim 1, wherein the intermediate conductor has a cylindrical shape, an I-shape, a cross shape, a square, a sheet shape, a ring shape or a tubular shape.

7. The graphene Nano-steam generator in claim 1, wherein all or part of the intermediate conductor is made of graphene, fullerene, carbon fiber, zinc, iron, platinum, titanium, copper, gold or silver.

8. The graphene Nano-steam generator in claim 1, wherein at least one of the first electrode, the second electrode, the intermediate conductor and the electrode fixing member is covered with felt or nonwoven fabrics.

* * * * *